United States Patent [19]

Ono et al.

[11] Patent Number: 5,117,034
[45] Date of Patent: May 26, 1992

[54] PHOSPHATIDYLSERINE DERIVATIVES

[75] Inventors: Mitsunori Ono; Hideto Mori, both of Kanagawa, Japan

[73] Assignee: Fuji Photo Film Co., Ltd., Kanagawa, Japan

[21] Appl. No.: 602,557

[22] Filed: Oct. 24, 1990

[30] Foreign Application Priority Data

Oct. 24, 1989 [JP] Japan .................. 1-276525
Oct. 25, 1989 [JP] Japan .................. 1-278013
Oct. 25, 1989 [JP] Japan .................. 1-278014
May 28, 1990 [JP] Japan .................. 2-137887

[51] Int. Cl.⁵ .................................. C07F 9/12
[52] U.S. Cl. .......................... 558/169; 558/172
[58] Field of Search .......................... 558/172, 169

[56] References Cited

FOREIGN PATENT DOCUMENTS 8910370 11/1989 World Int. Prop. O. .......... 558/172

Primary Examiner—Mary C. Lee
Assistant Examiner—Michael G. Ambrose
Attorney, Agent, or Firm—Sughrue, Mion, Zinn, Macpeak & Seas

[57] ABSTRACT

A phosphatidylserine derivative represented by formulae (I), (II), and (III):

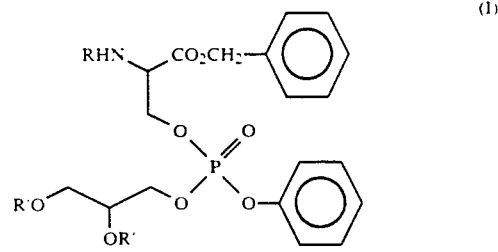

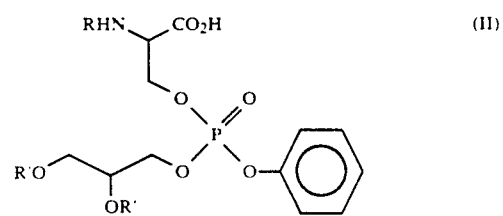

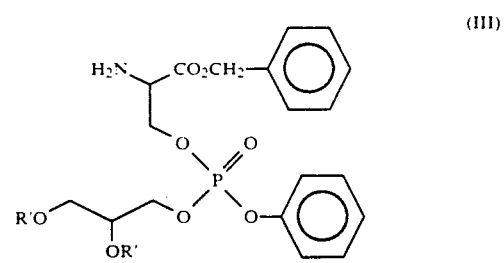

wherein R represents a protective group which can be removed by an acid; and R' represents a straight chain or branched alkyl group having from 8 to 24 carbon atoms and may contain a substituent group, or may be unsaturated, provided that if an asymmetric carbon is present, the phosphatidylserine derivative is a racemic mixture or an optically active isomer thereof. Preferably, R represents a tertiary butoxycarbonyl group; R' represents a straight chain or branched alkyl group having 14, 16, or 18 carbon atoms; and the substituent is an alkylcarbonyl group, an alkoxycarbonyl group, a halogen atom, or an aryl group.

15 Claims, 6 Drawing Sheets

PHOSPHATIDYLSERINE DERIVATIVES

FIELD OF THE INVENTION

This invention relates to a phosphatidylserine derivative useful as a precursor for a lipid membrane structural material for modifying the surface of a lipid bimolecular membrane such as a liposome.

BACKGROUND OF THE INVENTION

In order to strengthen the structure and modify the function of a lipid bimolecular membrane such as a liposome, surface reformation (modification) is an important consideration. Known methods of introducing a functional compound like a protein to a lipid bimolecular membrane such as a liposome involve using a non-covalent bond or using a covalent bond. Considering the strength of the bond and the stability of the membrane, among other things, the covalent bond method is more useful.

Generally, the method of using a covalent bond involves combining the surface of a lipid bimolecular membrane with a chosen molecule for forming a covalent bond using a divalent crosslinking agent and practically, an amino group or an SH group on a protein, or a sugar chain is utilized as a functional group for the bonding.

More specifically, a method of using an SH group involves a method of bonding using a maleinimido group as a crosslinking agent via a Michael addition reaction for the maleinimido group (*Biochimica et Biophysica Acta*, 943, 53 (1988)), a method of bonding an antibody activated by N-succinimidyl-3-(2-pyridyldithio)propionyl phosphatidylethanolamine and N-succinimidyl-3-(2-pyridyldithio) propionate (*Nature*, 288, 602 (1980)), and a method of bonding using an α-haloketone group as the crosslinking agent via a nucleophilic displacement reaction for the group (European Patent 0,312,212). A method of utilizing sugar chains involves a method of incorporating a glycolipid into the membrane side of the lipid bimolecular membrane, cutting the glycolipid with periodic acid, and reacting the aldehyde formed with an amino group (*Science*, 210, 539 (1980)).

However, these methods all require a considerable number of steps and they can only be used for specific reactions.

It is also known to add a functional group to a lipid bimolecular membrane such as a liposome using a single-strand lipid membrane structural material which can be easily synthesized, as disclosed in JP-A-61-112021, JP-A-62-201864, JP-A-62-209092, and JP-A-1-27637 (the term "JP-A" as used herein means an "unexamined published Japanese patent application"). However, since a single-strand lipid membrane structural material is a reverse corn type molecule wherein the hydrophilic portion is more bulky than the hydrophobic portion, it has a disadvantage of being easily released from the membrane component in which case it would become a membrane poison.

Thus, there is great demand for a lipid membrane structural material that can be easily used to modify the surface of a lipid bimolecular membrane, has a variety of applications, and is safe for living organisms.

SUMMARY OF THE INVENTION

An object of this invention is to provide a phosphatidylserine derivative which can easily modify a surface of a lipid bimolecular membrane and is safe for living organisms.

It has been discovered that this and other objects can be attained by a phosphatidylserine derivative represented by formulae (I), (II), or (III):

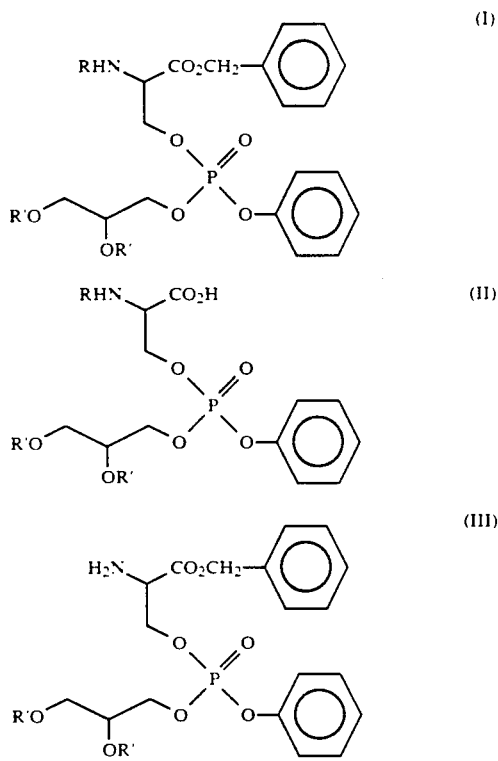

wherein R represents a protective group capable of being removed by an acid, (preferably a tertiary butoxycarbonyl group); R' represents a straight chain or branched acyclic hydrocarbon group having from 8 to 24 carbon atoms, (preferably having 14, 16 or 18 carbon atoms), and this group may have a substituent group or may be unsaturated. Examples of substituents are an alkylcarbonyl group, an alkoxycarbonyl group, a halogen atom, and an aryl group. If unsaturated, there may be a double bond or a triple bond, and there may be two or more such bonds in the same chain. If there is an asymmetric carbon in the molecule the derivative may be a racemic mixture or an optically active isomer thereof.

DETAILED DESCRIPTION OF THE INVENTION

Figure 1:
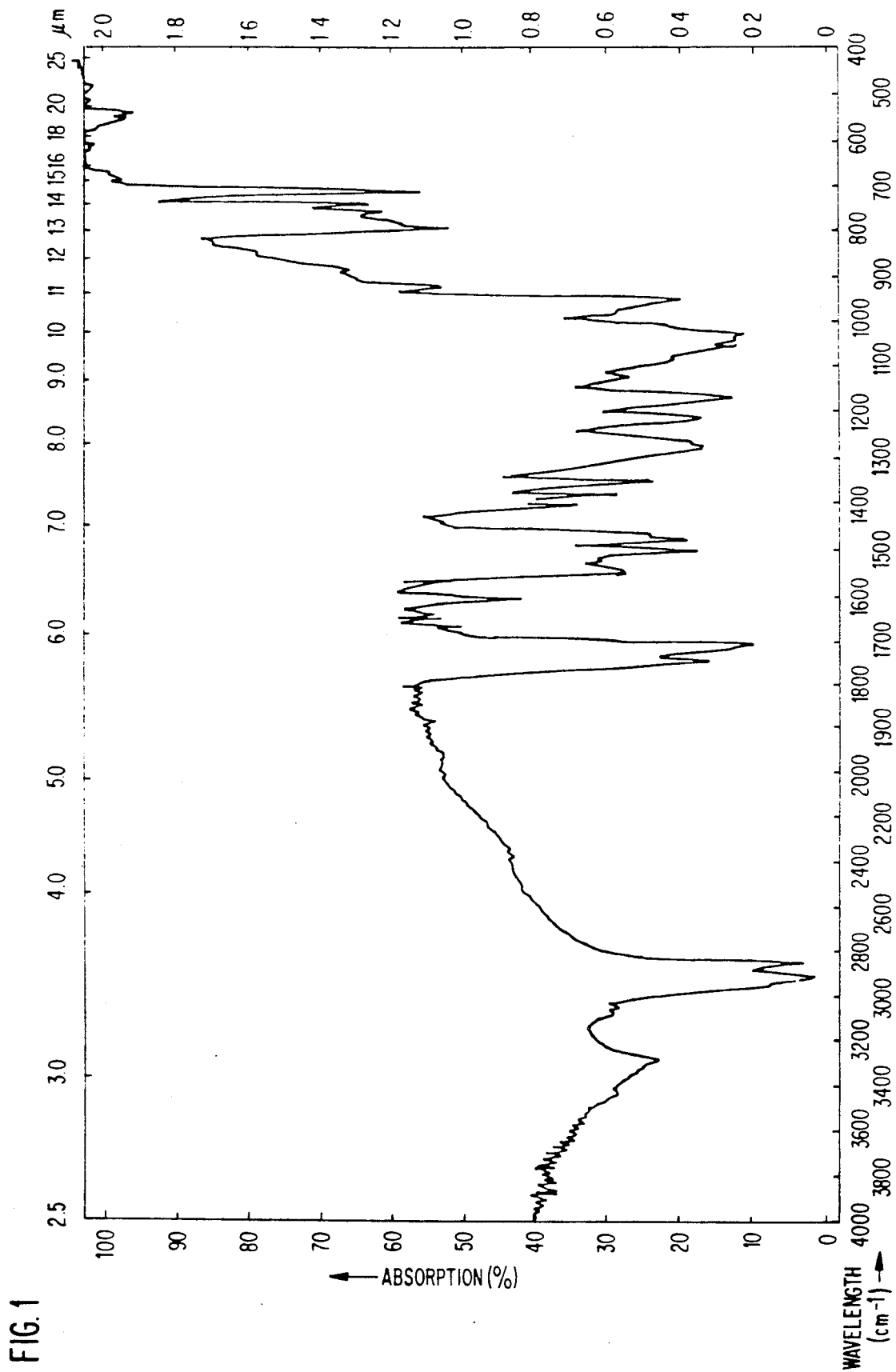
FIG. 1 is a graph of the infrared absorption spectrum, using a nujol paste method, of an optically active substance of a compound corresponding to formula (I) wherein R is a tertiary butoxycarbonyl group and R' is n—$C_{16}H_{33}$.
Figure 2:
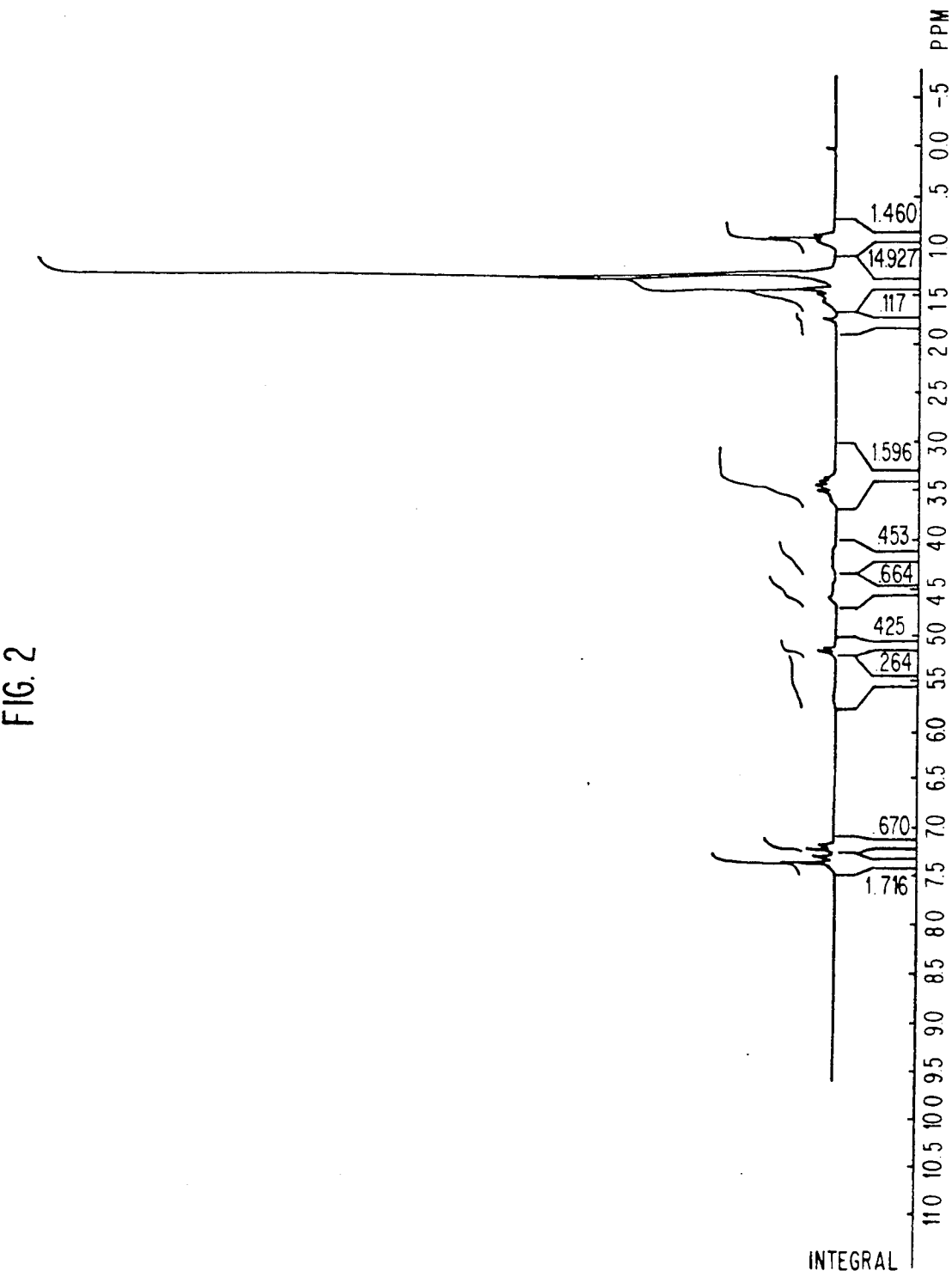
FIG. 2 is a graph of the 200 MHz proton nuclear magnetic resonance spectrum (solvent: $CDCl_3$, standard material: tetramethylsilane) of the compound analyzed in FIG. 1.
Figure 3:
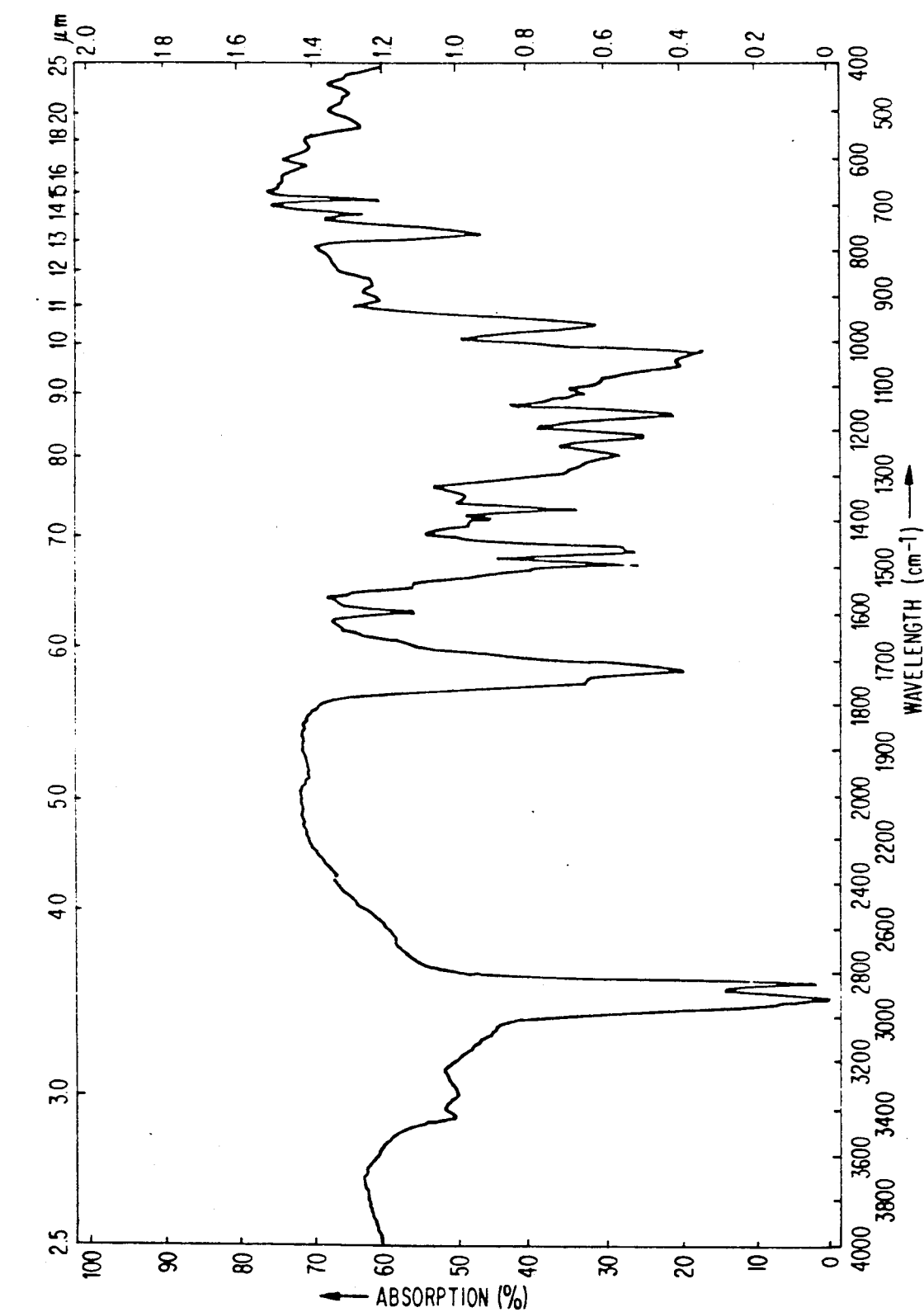
FIG. 3 is a graph of the infrared absorption spectrum, using a nujol paste method, of an optically active substance of a compound corresponding to formula (II) wherein R is a tertiary butoxycarbonyl group and R' is n—$C_{16}H_{33}$.
Figure 4:
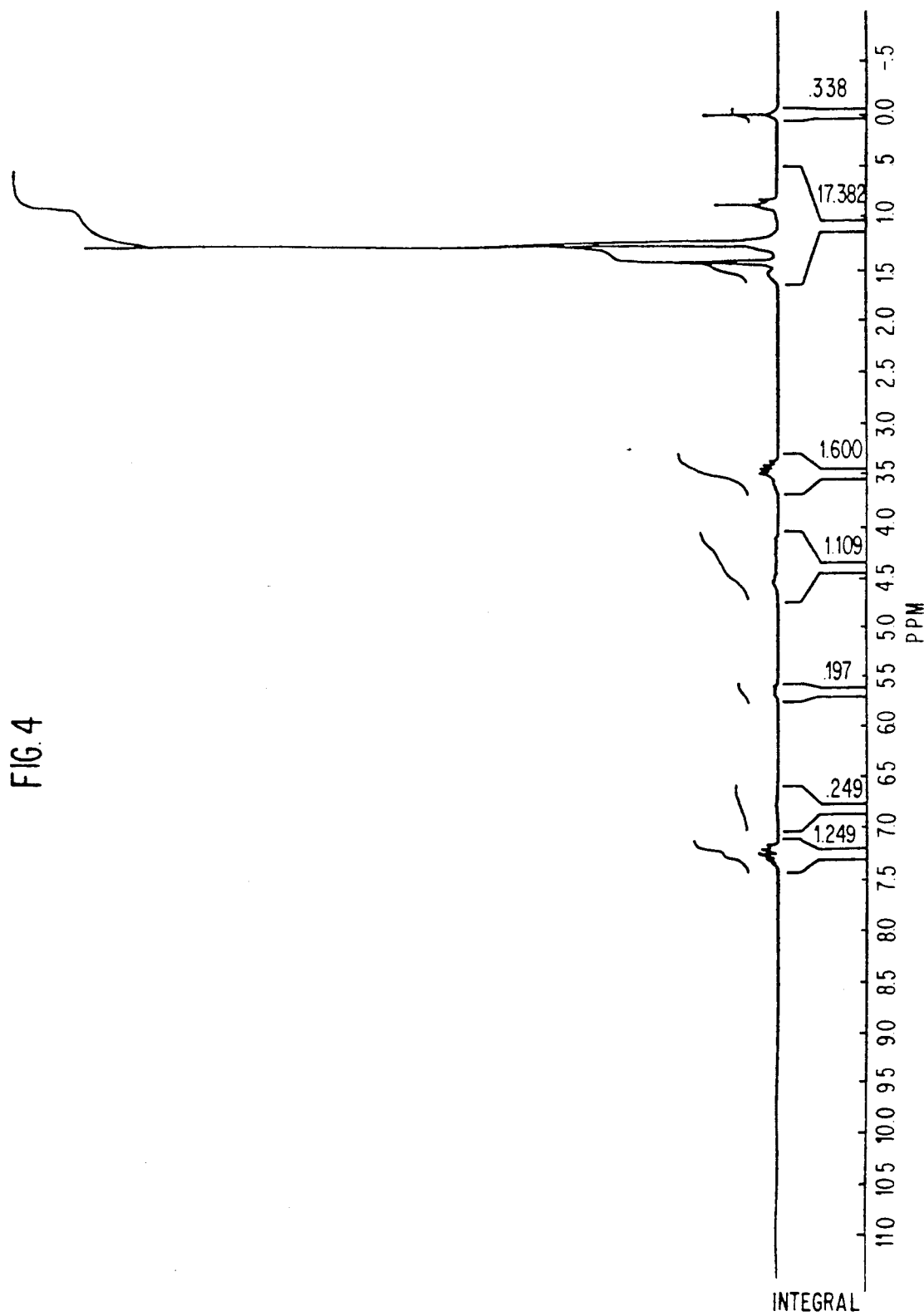
FIG. 4 is a graph of the 200 MHz proton nuclear magnetic resonance spectrum (solvent: CDCl₃, standard material: tetramethylsilane) of the compound analyzed in FIG. 3.
Figure 5:
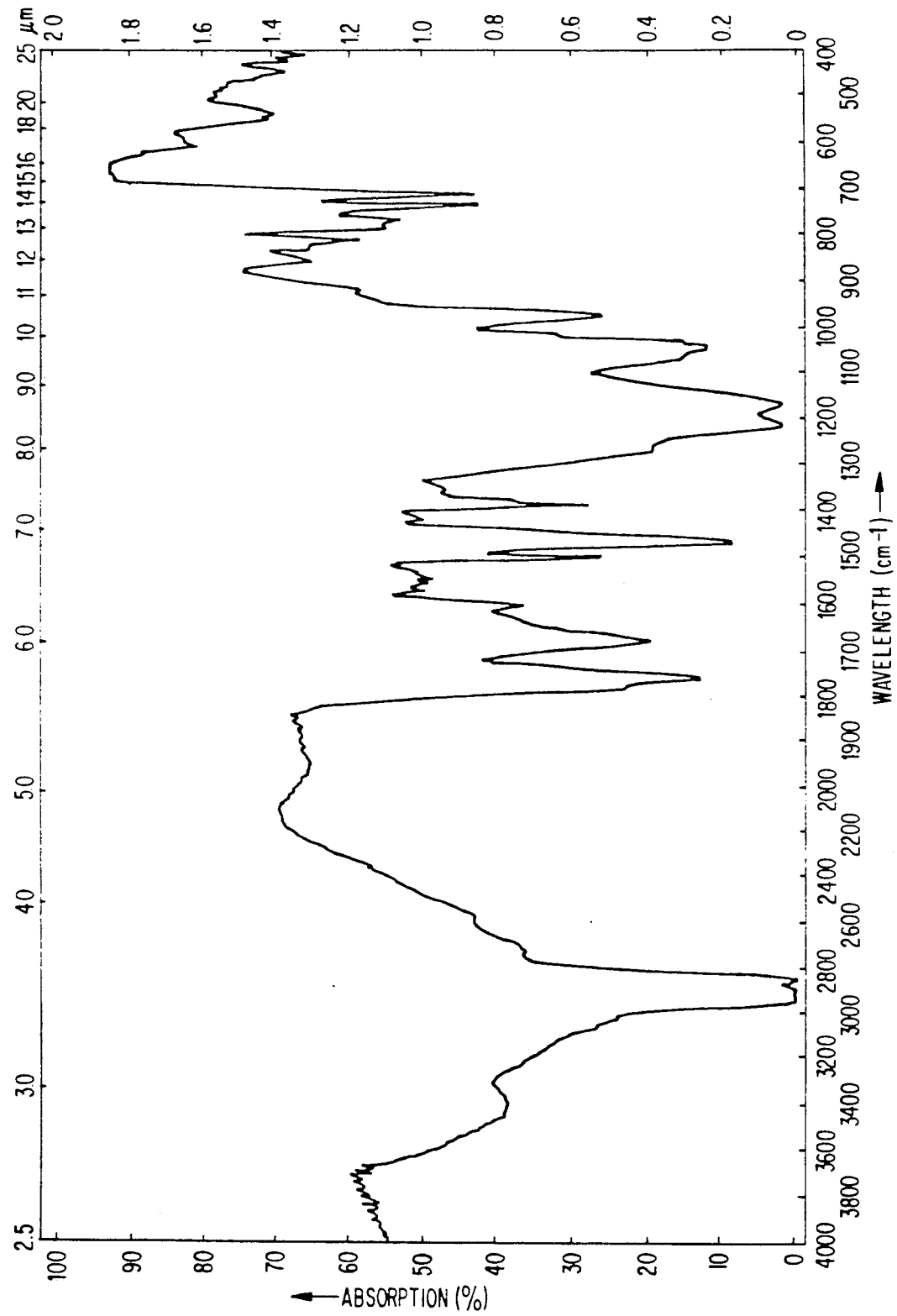
FIG. 5 is a graph of the infrared absorption spectrum of the trifluoroacetate of an optically active substance corresponding to formula (III) wherein R' is n—C₁₆H₃₃.
Figure 6:
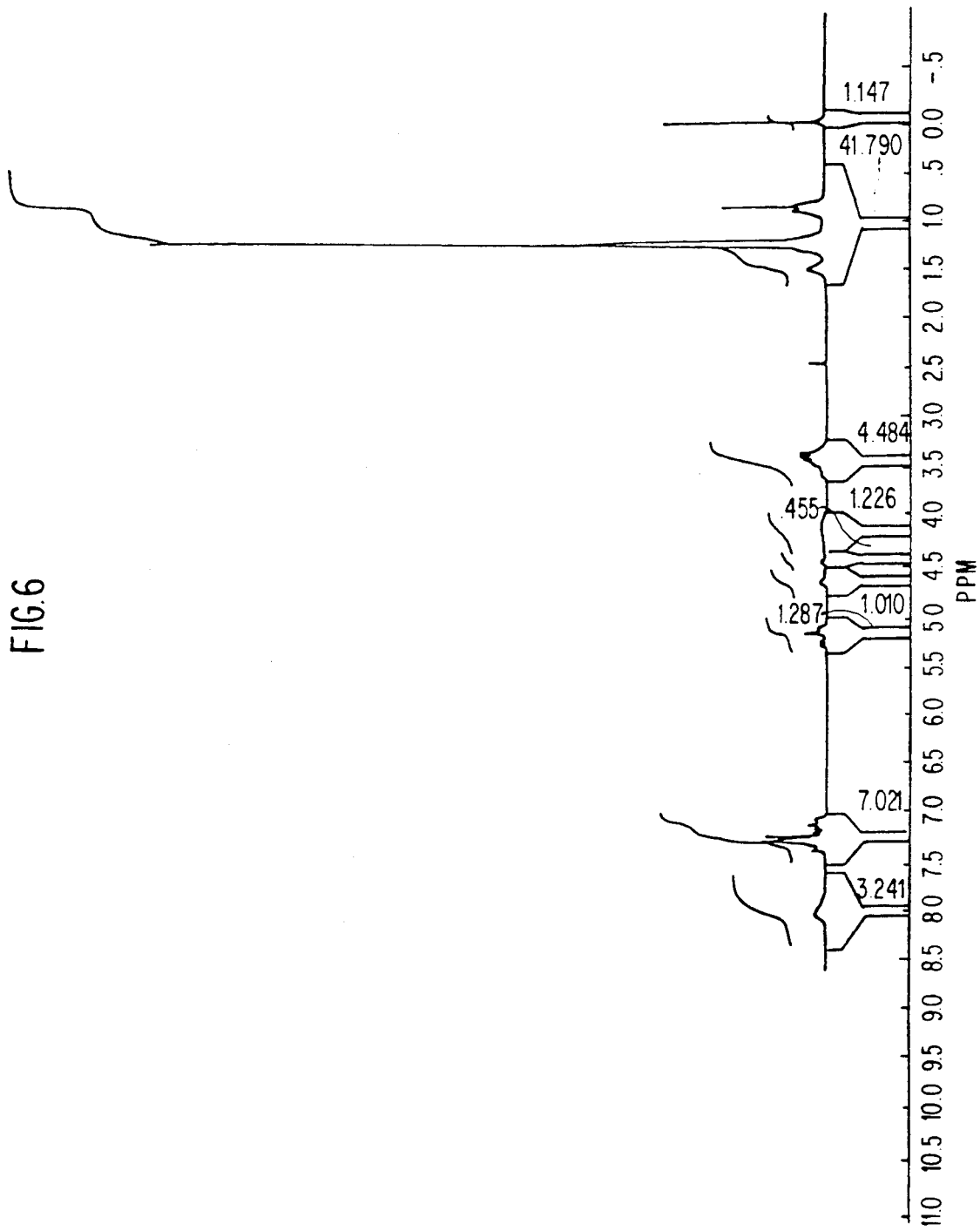
FIG. 6 is a graph of the 200 MHz proton nuclear magnetic resonance spectrum (solvent: CDCl₃, standard material: tetramethylsilane) of the compound analyzed in FIG. 5.

Examples of the syntheses of optically active compounds according to the invention are illustrated below, but these syntheses are not limiting.

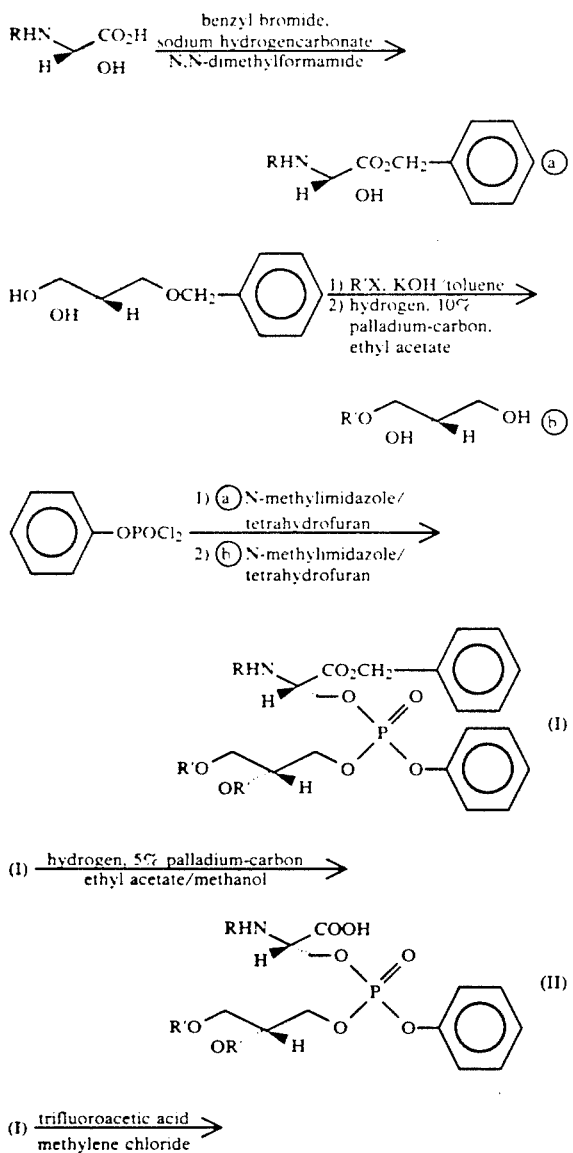

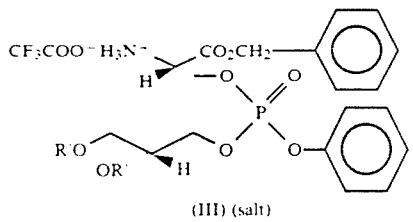

(III) (salt)

a chloroform solution of the above compound is prepared and washed with a saturated aqueous solution of sodium hydrogencarbonate.

(III) (free amino compound)

The amino group, the carboxy group, and the phosphoric acid group of the serine moiety of the compounds of the invention corresponding to formula (I) can be separately protected and also can be selectively deprotected without adversely affecting other functional groups.

When the carboxy group of the serine moiety of the compounds of the invention corresponding to formula (II) is in a free state, the amino and phosphoric acid groups thereof can be separately protected and also selectively deprotected without adversely affecting other functional groups.

When the amino group of the serine moiety of the compounds of this invention corresponding to formula (III) is in a state of high reactivity, the carboxy and phosphoric acid groups thereof can be separately protected and also selectively deprotected without adversely affecting other functional groups.

Compounds obtained by deprotecting a compound corresponding to formulae (I), (II), or (III) can form a lipid bimolecular membrane such as a liposome by themselves or by mixing them with other lipid membrane structural materials. Such compounds can have a positive, negative, or amphoteric charge. In addition, since serine, which is one of the constitutional components of the compound, is a naturally existing amino acid, these compounds are safe for living organisms.

Also, by bonding a functional compound such as an amino acid, peptide, protein, saccharide, polymerizable group, or spacer having a reactivity to one or both of the hydrophilic amino group or the carboxy group as a foothold, a lipid membrane structural material having functional properties can be obtained. The lipid membrane structure material of the invention can form a liquid bimolecular membrane such as a liposome by itself or when mixed with other types of lipid membrane structural material. Additionally, a surface modification or strengthening of the structure can be achieved in such a lipid bimolecular membrane.

It has recently been clarified that the saccharide existing at the surface of a cell membrane functions in intercellular information transfer, for example, and there is a possibility that a liposome can be targeted to a specific cell by the surface modification with saccharide.

Thus, the compounds of this invention are important as precursors for functional lipid membrane structural materials.

The invention is illustrated further with the non-limiting examples below. Unless otherwise indicated, all ratios and percentages are by weight.

EXAMPLE 1

Synthesis of an optically active compound of formula (I) when R is a tertiary butoxycarbonyl group and R' is n—$C_{16}H_{33}$:

A) Synthesis of (s)-N-t-Butoxycarbonylserine benzyl ester:

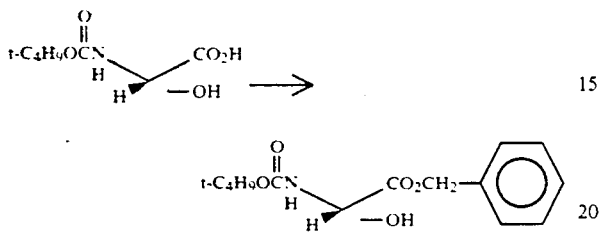

According to the method described in *Synthesis*, 961 (1979), this ester was obtained at a yield of 80% from (s)-N-t-butyoxycarbonylserine and benzyl bromide.

B) Synthesis of (s)-2,3-di-o-hexadecyl-1-glycerol:

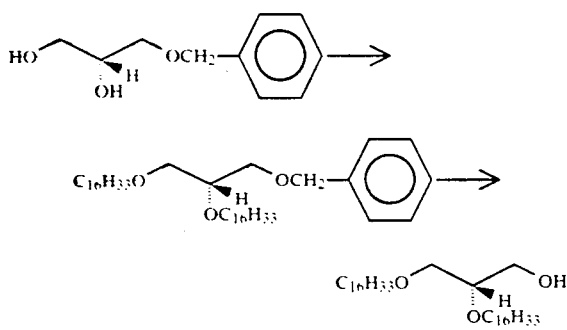

In 300 ml of toluene was dissolved 12.0 g of glycerol monobenzyl ether prepared by the method described in *Synthesis*, 503 (1985). After adding 16.0 g of powdery potassium hydroxide and 84.0 g of hexadecyl bromide to the solution, the reaction mixture was refluxed under heating for 8 hours. The reaction mixture was allowed to cool to room temperature and diluted with 400 ml of hexane. The reaction mixture was then washed twice with 200 ml of water and dried with anhydrous sodium sulfate. After removing the sodium sulfate by filtration, the filtrate was concentrated under reduced pressure to provide a colorless oily product.

The reaction mixture was purified by silica gel chromatography (eluent: hexane/ethyl acetate=40/1) to provide 41.2 g (yield 95.5%) of a dialkylglycerol monobenzyl ether compound.

The properties of the product coincided with described in *Biochemistry*, 2, 394 (1963).

The product was dissolved in 250 ml of ethyl acetate and after adding 1.5 g of 10% palladium-carbon, the mixture was reacted for 8 hours in a hydrogen atmosphere.

Insoluble matter was removed using sellite filtration and the sellite layer was washed with ethyl acetate. The filtrate was combined with the washed solution and the mixture was concentrated under reduced pressure. The residue thus formed was recrystallized from ethyl acetate to provide the desired compound as colorless crystals.

The properties of the product coincided with those described in *Biochemistry*, 2, 394 (1963).

C) Synthesis of an optically active compound of formula (I) when R is a tertiary butoxycarbonyl group and R' is n—$C_{16}H_{33}$:

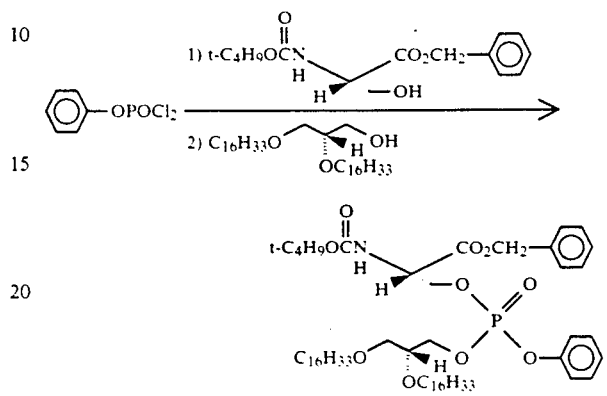

To a dry tetrahydrofuran solution of phenylphosphoro dichloridate ($PhOPOCl_2$, 2.75 g, commercially available product) was added 20 ml of a dry tetrahydrofuran solution of 2.95 g of (s)-N-t-butoxycarbonylserine benzyl ester and 1.07 g of N-methylimidazole over a period of 20 minutes. After stirring the reaction mixture for 10 minutes at room temperature, 20 ml of a dry tetrahydrofuran solution of 5.4 g of (s)-2,3-di-o-hexadecyl-1-glycerol and 1.07 g of N-methylimidazole was added thereto over a period of 10 minutes and the mixture was allowed to stand for 14 hours at room temperature.

The reaction mixture obtained was poured into 100 ml of water and extracted 4 times with 100 ml of chloroform. The organic layers (the extracts) were combined with each other, washed once with 150 ml of water, and dried with anhydrous sodium sulfate. The sodium sulfate was then removed by filtration and the filtrate was concentrated under reduced pressure to provide a colorless oily product.

The reaction mixture obtained was purified by silica gel chromatography (eluent: hexane/ethyl acetate =20/1 to 8/1) to provide 5.48 g (yield 56.3%) of the desired compound as a colorless waxy material.

The properties of the product are shown below.

IR $\nu$max (Nujol): 3260(m), 2930(s), 2860(s), 1745(s), 1705(s), 1600(m), 1495(m), 1270(s), 1210(s), 1165(s), 1065(s), and 1030(s) $cm^{-1}$.

$^1$H NMR $\delta$(200 MHz, solvent $CDCl_3$, standard substance TMS):
0.87(6H, deformed t, J=6 Hz), 1.25(54H, br s), 1.45(9H, s), 1.43-1.60(4H, br), 3.36-3.66(7H, m), 4.05-4.30(2H, m), 4.33-4.65(3H, m), 5.08-5.24(2H, m), 5.48-5.68(1H, m), 7.11-7.40(10H, m), and FAB-MS 974[(M+H)$^+$].

EXAMPLE 2

Following the method described in Example 1, except for the starting materials used, an optically active compound of formula (I) wherein R was a tertiary butoxycarbonyl group and R' was n—$C_{14}H_{29}$ or n—$C_{18}H_{37}$ was synthesized.

The properties of this compound are shown below.

A compound of formula (I) wherein R' was n—$C_{14}H_{29}$:

Elemental Analysis:

| | C | H | N |
|---|---|---|---|
| Found: | 68.31% | 9.61% | 1.50% |
| Calculated: | 68.05% | 9.60% | 1.53% |

A compound of formula (I) wherein R' was n—$C_{18}H_{37}$:

| | C | H | N |
|---|---|---|---|
| Found: | 69.86% | 10.06% | 1.41% |
| Calculated: | 69.97% | 10.11% | 1.36% |

EXAMPLE 3

Synthesis of an optically active compound of formula (II) wherein R is a tertiary butoxycarbonyl group and R' is n—$C_{16}H_{33}$:

In 10 ml of a mixed solvent of ethyl acetate and methanol (1:1) was dissolved 200 mg of compound obtained in C) of Example 1 and after adding thereto 10 mg of 5% palladium-carbon, the mixture was reacted for 7 hours at normal pressure in a hydrogen atmosphere.

Insoluble matter was removed by sellite filtration and the sellite layer was washed with ethyl acetate. The filtrate was combined with the washed solution and the mixture was concentrated under reduced pressure to provide 190 mg (quantitative) of the desired compound as a colorless waxy material.

The properties of the compound are shown below.

IR νmax (Nujol): 3600-3000(br m), 1725(s), 1600(m), 1500(s), 1255(s), 1210(s), 1170(s), 1060(s), 1030(s), and 960(s) cm$^{-1}$.

$^1$H NMR δ(200 MHz, solvent $CDCl_3$, standard material TMS):
0.88(6H, deformed t, J=6 Hz), 1.25(54H, br s), 1.43 and 1.66(9H, each s), 1.40-1.60(4H, m), 3.38-3.66(7H, m), 4.07-4.65(5H, m), 5.60-5.70(1H, m), 6.58-7.00(1H, br, COOH), 7.10-7.40(5H, m), and FAB-MS 906 [(M+Na)$^+$].

EXAMPLE 4

Following the method described in Example 3, except for the starting materials used, an optically active compound of formula (II) wherein R was a tertiary butoxycarbonyl group and R' was n—$C_{14}H_{29}$ or n—$C_{18}H_{37}$ was synthesized.

The properties of this compound are shown below.

A compound of formula (II) wherein R' was n—$C_{14}H_{29}$:

Elemental Analysis:

| | C | H | N |
|---|---|---|---|
| Found: | 65.26% | 9.94% | 1.63% |
| Calculated: | 65.30% | 9.92% | 1.69% |

A compound of formula (II) wherein R' was n—$C_{18}H_{37}$:

Elemental Analysis:

| | C | H | N |
|---|---|---|---|
| Found: | 69.56% | 10.41% | 1.37% |
| Calculated: | 67.73% | 10.44% | 1.49% |

EXAMPLE 5

Synthesis of the trifluoroacetate of an optically active compound of formula (III) wherein R' is n—$C_{16}H_{33}$:

After adding 10 ml of trifluoroacetic acid (commercially available product) to 10 ml of a methylene chloride solution of 1.0 g of compound obtained in C) of Example 1, the mixture was stirred for 20 minutes at room temperature.

The reaction mixture was concentrated under reduced pressure to provide an oily product which was dried under reduced pressure to provide 1.05 g (quantitative) of the desired compound as a colorless waxy material.

The properties thereof are shown below.

IR νmax (Nujol): 3600-3000(br), 2740-2200(br), 1765(s), 1675(s), 1600(m), 1500(m), 1215(s), 1170(s), and 1.040 cm$^{-1}$.

$^1$H NMR δ(200 MHz, solvent $CDCl_3$, standard material TMS):
0.87(6H, deformed t, J=6 Hz), 1.25(54H, br s), 1.40-1.60(4H, m), 3.35-3.63(7H, m), 4.00-4.30(2H, m), 4.40-4.50(1H, m), 4.59-4.64(2H, m), 5.13-5.21(2H, m), 7.07-7.43(10H, m), and 7.80-8.20(3H, amino group exchanging proton).

Elemental Analysis:

| | C | H | N |
|---|---|---|---|
| Found: | 64.21% | 9.18% | 1.41% |
| Calculated: | 64.43% | 9.02% | 1.42% |

EXAMPLE 6

Following the method described in Example 5, except for the starting materials used, a trifluoroacetate of an optically active compound of formula (III) wherein R' was n—$C_{14}H_{29}$ or n—$C_{18}H_{37}$ was synthesized.

The properties thereof are shown below.

Compound of formula (III) wherein R' was n—$C_{14}H_{29}$:

Elemental Analysis:

| | C | H | N |
|---|---|---|---|
| Found: | 62.99% | 8.61% | 1.43% |
| Calculated: | 63.16% | 8.70% | 1.50% |

Compound of formula (III) wherein R' was n—$C_{18}H_{37}$:

Elemental Analysis:

| | C | H | N |
|---|---|---|---|
| Found: | 65.53% | 9.15% | 1.42% |
| Calculated: | 65.58% | 9.30% | 1.34% |

While the invention has been described in detail and with reference to specific embodiments thereof, it will be apparent to one skilled in the art that various changes and modifications can be made therein without departing from the spirit and scope thereof.

What is claimed is:

1. A phosphatidylserine derivative represented by formula (I):

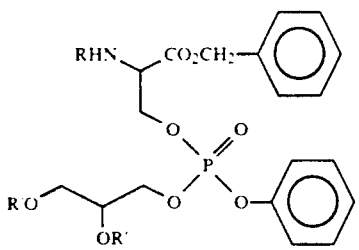

(I)

wherein R represents a tertiary butoxycarbonyl group which can be removed with an acid; and R' represents a straight chain or branched acyclic hydrocarbon group having from 8 to 24 carbon atoms, and may have a substituent group, wherein said substituent group is an alkylcarbonyl group or alkoxycarbonyl group, or may be unsaturated, provided that if an asymmetric carbon is present, said phosphatidylserine derivative is a racemic mixture or an optically active isomer thereof.

2. A phosphatidylserine derivative represented by formula (II):

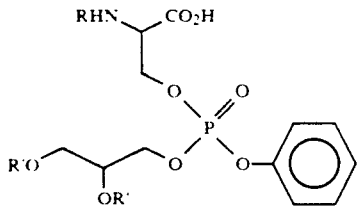

(II)

wherein R represents a tertiary butoxycarbonyl group which can be removed with an acid; and R' represents a straight chain or branched acyclic hydrocarbon group having from 8 to 24 carbon atoms, and may have a substituent group, wherein said substituent group is an alkylcarbonyl group or alkoxycarbonyl group, or may be unsaturated, provided that if an asymmetric carbon is present, said phosphatidylserine derivative is a racemic mixture or an optically active isomer thereof.

3. A phosphatidylserine derivative represented by formula (III):

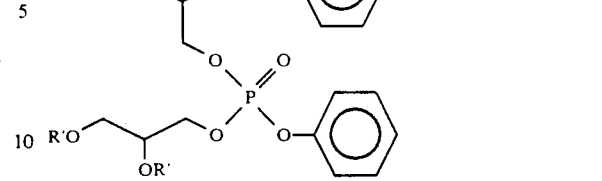

(III)

wherein R' represents a straight chain or branched acyclic hydrocarbon group having from 8 to 24 carbon atoms, and may have a substituent group, wherein said substituent group is an alkylcarbonyl group or alkoxycarbonyl group, or may be unsaturated, provided that if an asymmetric carbon is present, said phosphatidylserine derivative is a racemic mixture or an optically active isomer thereof.

4. A phosphatidylserine derivative as claimed in claim 1, wherein R' represents a straight chain or branched alkyl group having 14, 16, or 18 carbon atoms.

5. A phosphatidylserine derivative as claimed in claim 1, wherein said acyclic hydrocarbon group contains at least one double bond.

6. A phosphatidylserine derivative as claimed in claim 1, wherein said acyclic hydrocarbon group contains at least one triple bond.

7. A phosphatidylserine derivative as claimed in claim 1, wherein said acyclic hydrocarbon group contains a combination of double and triple bonds.

8. A phosphatidylserine derivative as claimed in claim 2, wherein R' represents a straight chain or branched acyclic hydrocarbon group having 14, 16, or 18 carbon atoms.

9. A phosphatidylserine derivative as claimed in claim 2, wherein said acyclic hydrocarbon group contains at least one double bond.

10. A phosphatidylserine derivative as claimed in claim 2, wherein said acyclic hydrocarbon group contains at least one triple bond.

11. A phosphatidylserine derivative as claimed in claim 2, wherein said acyclic hydrocarbon group contains a combination of double and triple bonds.

12. A phosphatidylserine derivative as claimed in claim 3, wherein R' represents a straight chain or branched acyclic hydrocarbon group having 14, 16, or 18 carbon atoms.

13. A phosphatidylserine derivative as claimed in claim 3, wherein said acyclic hydrocarbon group contains at least one double bond.

14. A phosphatidylserine derivative as claimed in claim 3, wherein said acyclic hydrocarbon group contains at least one triple bond.

15. A phosphatidylserine derivative as claimed in claim 3, wherein said acyclic hydrocarbon group contains a combination of double and triple bonds.

* * * * *